US012704573B2

(12) United States Patent
Sadleir

(10) Patent No.: US 12,704,573 B2
(45) Date of Patent: Aug. 11, 2026

(54) SYSTEMS AND METHODS FOR MULTIFREQUENCY MAGNETIC RESONANCE ELECTRICAL IMPEDANCE TOMOGRAPHY

(71) Applicant: Arizona Board of Regents on behalf of Arizona State University, Scottsdale, AZ (US)

(72) Inventor: Rosalind Sadleir, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 18/713,932

(22) PCT Filed: Dec. 6, 2022

(86) PCT No.: PCT/US2022/080993
§ 371 (c)(1),
(2) Date: May 28, 2024

(87) PCT Pub. No.: WO2023/107927
PCT Pub. Date: Jun. 15, 2023

(65) Prior Publication Data

US 2025/0020747 A1 Jan. 16, 2025

Related U.S. Application Data

(60) Provisional application No. 63/286,214, filed on Dec. 6, 2021.

(51) Int. Cl.
*G01R 33/48* (2006.01)
*A61B 5/00* (2006.01)
(Continued)

(52) U.S. Cl.
CPC ........ *G01R 33/4808* (2013.01); *A61B 5/0035* (2013.01); *A61B 5/0536* (2013.01); *A61B 5/055* (2013.01)

(58) Field of Classification Search
CPC .............................. A61B 5/0536; A61B 5/055
See application file for complete search history.

(56) References Cited

U.S. PATENT DOCUMENTS 6,397,095 B1 5/2002 Eyuboglu
2015/0245784 A1* 9/2015 Park ........................ A61B 5/055 600/411
2016/0143540 A1 5/2016 Gencer

FOREIGN PATENT DOCUMENTS

WO 2017007282 1/2017

OTHER PUBLICATIONS

"Magnetic flux density measurement in magnetic resonance electrical impedance tomography using a low-noise current source" by Y.T. Kim et al. Meas. Sci. Tech. 22. 2011.*

(Continued)

*Primary Examiner* — Jason M Ip
(74) *Attorney, Agent, or Firm* — Riverside Law LLP

(57) ABSTRACT

Disclosed herein are systems and methods for Magnetic Resonance Electrical Impedance Tomography (MREIT). A system for imaging biological tissue comprises a controller, a multifrequency arbitrary-waveform constant-current source, a Howland constant-current source, and a digital-to-analog converter. The controller is configured to generate a multifrequency magnetic resonance electrical impedance tomography sequence. The generation comprises producing, by the controller, a digital sequence, and converting, by the digital-to-analog converter, the digital sequence to an analog sequence. The generation may further comprise: producing, by the Howland constant-current source, a standard magnetic resonance electrical impedance tomography sequence (Continued)

based on the analog sequence; producing, by the multifrequency arbitrary-waveform constant-current source, a sine wave at one or more predetermined frequencies; and modulating the standard magnetic resonance electrical impedance tomography sequence with the sine wave. A method of measuring an electrical property of a biological tissue comprises imaging the biological tissue using this system.

20 Claims, 10 Drawing Sheets

(51) Int. Cl.
*A61B 5/0536* (2021.01)
*A61B 5/055* (2006.01)

(56) References Cited

OTHER PUBLICATIONS

"Resolution and Contrast in Magnetic Resonance Electrical Impedance Tomography (MREIT) and its Application to Cancer Imaging" by L. T. Muftuler et al. Tech. Canc. Res. Treat. Vol. 3, No. 6. 2004.*
Adrian, D.J. Auditory and visual sensations stimulated by low-frequency electric currents. Radio Science 12, 243-250 (1977).
Bhatia, T., et al. Preparing giant unilamellar vesicles (GUVs) of complex lipid mixtures on demand: Mixing small unilamellar vesicles of compositionally heterogeneous mixtures. Biochimica et Biophysia Acta 1848, 3175-3180 (2015).
Brown, B.H., Tidy, J.A., Boston, K. & Blackett, A.D. Relation between tissue structure and imposed electrical current flow in cervical neoplasia. Lancet 355, 892-895 (2000).
Butson, C.R. & Mcintyre, C.C. Tissue and electrode capacitance reduce neural activation vols. during deep brain stimulation. Clinical Neurophysiology 116, 2490-2500 (2005).
Chauhan, M., et al. Low-Frequency Conductivity Tensor Imaging of the Human Head in vivo using DTMREIT: First Study. IEEE Transactions on Medical Imaging 37, 966-976 (2018).
Chauhan, M., Vidya Shankar, R., Ashok Kumar, N., Kodibagkar, V. & Sadleir, R.J. Multi-shot echoplanar MREIT for fast imaging of conductivity, curent density and electric field distributions. Magnetic Resonance in Medicine 79, 71-82 (2018b).
Chiapperino, M. A., Mescia, L., Bia, P., Starešinič, B., Čemažar, M., Novickij, V., . . . & Miklavčič, D. (2020). Experimental and numerical study of electroporation induced by long monopolar and short bipolar pulses on realistic 3D irregularly shaped cells. IEEE Transactions on Biomedical Engineering, 67(10), 2781-2788.
Delaney, G.W. & Cleary, P.W. The packing properties of superellipsoids. Europhysics Letters 89, 34002 (2010).
Fabritius, G., et al. Cumulative radiation exposure from imaging procedures and associated lifetime cancer risk for patients with lymphoma. Scientific Reports 6, 35181 (2016).
Gabriel, C., Gabriel, S. & Corthout, E. The dielectric properties of biological tissues: I. Literature survey. Physics in medicine and biology 41, 2231-2249 (1996).
Gabriel, C., Peyman, A. & Grant, E.H. Electrical conductivity of tissue at frequencies below 1 MHz. Physics in Medicine & Biology 54, 4683-4878 (2009).
Gabriel, S., Lau, R.W. & Gabriel, C. The dielectric properties of biological tissues: II. Measurements in the frequency range 10 Hz to 20 GHz. Physics in medicine and biology 41, 2251-2269 (1996).
Gabriel, S., Lau, R.W. & Gabriel, C. The dielectric properties of biological tissues: III Parametric models for the dielectric spectrum of tissues. Physics in medicine and biology 41, 2271-2293 (1996).
Haemmerich, D., Schutt, D.J., Wright, A.S., Webster, J.G. & Mahvi, D.M. Electrical conductivity measurement of excised human metastatic liver tumours before and after thermal ablation. Physiological Measurement 30, 459-466 (2009).
Indahlastari, A., et al. Methods to Compare Predicted and Observed Phosphene Experience in tACS Subjects. Neural Plasticity (2018).
Kanal, E., Maravilla, K. & Rowley, H.A. Gadolinium contrast agents for CNS Imaging: Current Concepts and Clinical Evidence. American Journal of Neuroradiology 35, 2215-2226 (2014).
Kasinadhuni, A.K., et al. Imaging of Current Flow in the Human Head During Transcranial Electrical therapy. Brain Stimulation 10, 764-772 (2017b).
Kasinadhuni, A.K., Indahlastari, A., Chauhan, M., Mareci, T.H. & Sadleir, R.J. Comparisons between invivo current density images and computational models in human tACS recipients. Brain Stimulation 10, e30-e31 (2017).
Kim, S.-Y., et al. Correlation between electrical conductivity and apparent diffusion coefficient in breast cancer: effect of necrosis on magnetic resonance imaging. European Radiology 28, 3204-3214 (2018).
Kirson, E.D., et al. Alternating electric fields arrest cell proliferation in animal tumor models and human brain tumors. Proceedings of the National Academy of Science USA 104, 10152-10157 (2007).
Kirson, E.D., et al. Disruption of cancer cell replication by alternating electric fields. Cancer Research 64, 3288-3295 (2004).
Laufer, S., Ivorra, A., Reuter, V.E., Rubinsky, B. & Solomon, S.B. Electrical impedance characterization of normal and cancerous human hepatic tissue. Physiological Measurement 31, 995-1009 (2010).
Minhas, A.S., Chauhan, M., Fu, F. & Sadleir, R.J. Evaluation of Magnetohydrodynamic Effects in Magnetic Resonance Electrical Impedance Tomography at Ultra-high Magnetic Fields. Magnetic Resonance in Medicine 81, 2264-2276 (2018).
Mori, N., et al. Diagnostic value of electric properties tomography (EPT) for differentiating benign frommalignant breast lesions: comparison with standard dynamic contrast-enhanced MRI. European Radiology 29, 1778-1786 (2019).
Moscho, A., Orwar, O., Chiu, D.T., Modi, B.P. & Zare, R.N. Rapid preparation of giant unilamellar vesicles. Proceedings of the National Academy of Science USA 93, 11443-11447 (1996).
Nam, H.S., I., L.B., Choi, J., Park, C. & Kwon, O. Conductivity imaging with low level current injectionusing transversal J-substitution algorithm in MREIT. Physics in medicine and biology 52, 6717-6730 (2007).
Oh, T.I., et al. Noise analysis in fast magnetic resonance electrical impedance tomography (MREIT)based on spoiled multi gradient echo (SPMGE) pulse sequence. Physics in medicine and biology 59, 4723-4738 (2014).
Sadleir, R.J., et al. High field MREIT: setup and tissue phantom imaging at 11 T. Physiological Measurement 27, S261-S270 (2006).
Sadleir, R.J., et al. Noise analysis in magnetic resonance electrical impedance tomography at 3 and 11T field strengths. Physiological Measurement 26, 875-884 (2005).
Sajib, S.Z.K., Kim, H.J., Kwon, O. & Woo, E.J. Regional absolute conductivity reconstruction using projected current density in MREIT. Physics in medicine and biology 57, 5841-5859 (2012).
Sajib, S.Z.K., Kwon, O., Kim, H.J. & Woo, E.J. Electrodeless conductivity tensor imaging using MRI: basic theory and animal experiments. Biomedical Engineering Letters 8, 273-282 (2018).
Schwan, H.P. Electrical properties of tissue and cell suspensions. in Advances in biological and medical physics (ed. J.H. Lawrence & C.A. Tobias) 147-209 (1957).
Semmineh, N.B., et al. Assessing tumor cytoarchitecture using multiecho DSC-MRI derived measures of the transverse relaxivity at tracer equilibrium (TRATE). Magnetic Resonance in Medicine 74, 772-784 (2015).
Seo, J.K. & Woo, E.J. Electrical tissue property imaging at low frequency using MREIT. IEEE Transactions on Biomedical Engineering 61, 1390-1399 (2014).
Surowiec, A.J., Stuchly, S.S., Barr, J.R. & Swarup, A. Dielectric properties of breast carcinoma and the surrounding tissues. IEEE Transactions on Biomedical Engineering 35, 257-263 (1988).
Tha, K.K., et al. Noninvasive electrical conductivity measurement by MRI: a test of its validity and the electrical conductivity characteristics of glioma. European Radiology 28, 348-355 (2018).
Tsai, J.Z., et al. Dependence of apparent resistance of four-electrode probes on insertion depth. IEEE Transactions on Biomedical Engineering 47, 41-48 (2000).

(56) References Cited

OTHER PUBLICATIONS

Tuch, D.S., Wedeen, V.J., Dale, A.M., George, U.S. & Belliveau, J.W. Conductivity tensor mapping of the human brain using diffusion tensor MRI. Proceedings of the National Academy of Science USA 98, 11697-11701 (2001).
Tucker, A., Fox, R.M. & Sadleir, R.J. Biocompatible, high precision, wideband, improved Howland current source with lead-lag compensation. IEEE Transactions on Biomedical Circuits and Systems 7, 63-70 (2012).
Voigt, T., Katscher, U. & Doessel, O. Quantative conductivity and permittivity imaging of the human brain using electric properties tomography. Magnetic Resonance in Medicine 66, 456-466 (2011).
Weaver, J.C. & Shoenbach, K.H. Biodielectrics. IEEE Transactions on Dielectrics and Electrical Insulation 10, 715-716 (2003).
Wenger, C., Hershkovich, H.S., Tempel-Brami, C., Giladi, M. & Bomzon, Z. Water-content electrical property tomography (wEPT) for mapping brain tissues' conductivity in the 200-1000 KHz range: Results of an animal study. in Brain and Human Body Modeling: Computational Human Modeling at EMBC 2018 (ed. S. Makarov, M. Horner & G. Noetscher) 367-393 (Springer, 2019).

* cited by examiner

SYSTEMS AND METHODS FOR MULTIFREQUENCY MAGNETIC RESONANCE ELECTRICAL IMPEDANCE TOMOGRAPHY

CROSS-REFERENCE TO RELATED APPLICATIONS

This application is a U.S. national phase application filed under 35 U.S.C. § 371 claiming benefit to International Patent Application No. PCT/US2022/080993, filed Dec. 6, 2022, which is entitled to priority of U.S. Provisional Patent Application No. 63/286,214, filed on Dec. 6, 2021, the contents of which are each incorporated by reference herein in their entirety.

STATEMENT REGARDING FEDERALLY SPONSORED RESEARCH OR DEVELOPMENT

This invention was made with government support under R21 EB030858 awarded by the National Institutes of Health. The government has certain rights in the invention.

TECHNICAL FIELD

The present disclosure relates generally to systems and methods for Magnetic Resonance Electrical Impedance Tomography (MREIT) at frequencies that aid in the diagnosis and therapy of cancers, among other applications.

BACKGROUND OF THE INVENTION

The overall rate of brain cancer in the US is 6.3 cases per 100,000 people. Glioblastoma Multiforme (GBM) is the most common and deadly form of brain cancer in adults (about 15% of cases), with most of those diagnosed surviving only around 15 months. Treatment for GBM typically involves surgery, radiotherapy, and chemotherapy with temozolomide. Recently, tumor treating fields (TTFields) combined with chemotherapy have been found to improve patient prognoses. TTFields treatments comprise alternating electric fields applied to the scalp via insulated electrodes at frequencies around 200 kHz, and electric fields of about 2 V/cm. It has been hypothesized that the mechanism of action for TTFields is disruption of cell division. Enhanced understanding of the TTFields mechanism, as well as treatment planning and monitoring, require detailed knowledge of electrical properties below 500 kHz. There is therefore a specific, urgent need for noninvasive methods to map conductivity distributions in this range for treatment planning and mechanism determination. Diagnosis and monitoring of cancer typically involves use of Gadolinium (Gd) contrast or ionizing radiation (CT, PET), each of which involves additional risk, especially if used repeatedly. Thus, safe methods of detecting, characterizing and monitoring tumors is of great interest.

The electrical conductivity and permittivity of tissues are highly sensitive to ionic concentration and mobility, membrane density and thickness, temperature, cell size, and distribution. Contrasts vary over several orders of magnitude. While there is a long history of measuring electrical properties, the range between DC and about 1 MHz is relatively unexplored. Electrical properties below 1 MHz determine how the body conducts endogenous electrical signals generated by the brain, peripheral nerves, or heart, and distributions of externally applied electricity in electroconvulsive therapy, deep brain stimulation, transcranial stimulation, electrocautery, electroporation, and hyperthermic cancer treatment. Despite their biological relevance, properties below 1 MHz are difficult to obtain because they must be measured via direct electrode-tissue contact, limiting in vivo utility. Therefore, many values in the existing literature have been obtained using bulk excised tissue samples or, if in vivo, during invasive procedures on animals. Moreover, electrode-based measurements depend on sample or electrode shape or application pressure. Consequently, most conductivity and permittivity spectra have been measured at frequencies above 1 MHz.

Tumor and cancer cell properties in the 10 to 100 kHz range differ from normal tissues because of changes in cell size, morphology, and membrane properties. Higher permittivity and conductivities than normal tissues have been measured in tumors of several types, with higher conductivities believed to be associated with the larger water content, increased vascularization, and changes in membrane permeability and cell density of neoplastic tissue. Existing investigations of glioma electrical properties have been performed at DC or between 5 and 500 MHz, but no indications of properties in the intermediate range are available. Mapping electrical properties of different tumor tissue types, and determining their spectral dependence, will improve treatment planning and monitoring of tumor regions safely, and with higher or complementary sensitivities to presently available imaging techniques.

Three MR-based techniques can be used to image electrical properties in vivo. Electric Properties Tomography (EPT) can measure conductivity at the Larmor frequency of the MRI system used (around 128 MHz for 3 T systems) without the need to apply external currents. Such EPT images do not reflect membrane properties but illustrate ionic mobilities and distributions. Nonetheless, EPT images at 128 MHz have been used to inform TTFields research as well as being tested in diagnosis and surgical planning in both glioblastoma and breast cancer. Another method, Conductivity Tensor Imaging (CTI), combines multiple diffusion and EPT measurements to determine intra- and extracellular conductivities and cell fractions, without the need to inject current, but only reflects static properties.

The third method, Magnetic Resonance Electrical Impedance Tomography (MREIT), can currently only be used to image electrical properties below 100 Hz. MREIT methods have been developed to non-invasively image current density and anisotropic conductivity distributions within the body using magnetic flux densities caused by electrical current flow. In existing MREIT applications, tissue properties are measured at frequencies below 100 Hz. This type of MREIT information is potentially of great utility in characterizing tissue electrical properties at the low frequencies characteristic of brain and cardiac activity. However, knowledge of tissue electrical conductivity dependence below 1 MHz would allow improved understanding of the biophysics underlying these properties, and may ultimately result in greatly improved sensitivity and specificity in planning and monitoring electrical therapies, including electroporation and transcranial electrical stimulation, and potentially in diagnosing cancer or ischemic stroke.

Unfortunately, relatively few reports of tissue electrical properties are in the 100 Hz to 1 MHz frequency range, because they involve invasive and often error-prone procedures. Several Magnetic Resonance Imaging (MRI)-based, non-invasive methods of imaging electrical property distributions have recently been developed. However, these methods can only be used at high frequencies (>100 MHz) or very low frequencies (<100 Hz). For example, the technique of Diffusion Tensor Magnetic Resonance Electrical Impedance Tomography (DT-MREIT) combines MR diffusion tensor and MR phase images to produce reconstruction of full anisotropic conductivity tensor images at very low frequencies. However, present DT-MREIT techniques are restricted to measurement frequencies of around 10 Hz. Therefore, a non-invasive method of MREIT is needed for measuring the electrical properties of tissue in the 100 Hz to 1 MHz frequency range.

SUMMARY OF THE INVENTION

Some embodiments of the invention disclosed herein are set forth below, and any combination of these embodiments (or portions thereof) may be made to define another embodiment.

Disclosed herein are systems and methods for multifrequency Magnetic Resonance Electrical Impedance Tomography (MF-MREIT). In an embodiment, a system for imaging biological tissue may comprise a controller, a multifrequency arbitrary-waveform constant-current source, a Howland constant-current source, and a digital-to-analog converter. The controller may be configured to generate a multifrequency magnetic resonance electrical impedance tomography sequence. In an embodiment, the generation may comprise producing, by the controller, a digital sequence, and converting, by the digital-to-analog converter, the digital sequence to an analog sequence. The generation may further comprise producing, by the Howland constant-current source, a standard magnetic resonance electrical impedance tomography sequence based on the analog sequence. The generation may still further comprise producing, by the multifrequency arbitrary-waveform constant-current source, a sine wave at one or more predetermined frequencies. The generation may also comprise modulating the standard magnetic resonance electrical impedance tomography sequence with the sine wave.

In an embodiment, the system further comprises a magnetic resonance imaging system, wherein the magnetic resonance imaging system is configured to produce a measurable signal based on the multifrequency magnetic resonance electrical impedance tomography sequence.

In an embodiment, the measurable signal is interpreted using Bloch equations, wherein the Bloch equations are modified to include effects of external currents.

In an embodiment, the modified Bloch equations are defined by $$S(k_x, k_y) = \int\int_{\Omega_{z_0}} M(x, y) e^{i[\gamma T_c B_z(x,y)]} e^{-i2\pi(k_x x + k_y y)} dxdy,$$

where M(x,y)>0 is the MR magnitude image of the slice Q located at $z_0$, δ(x,y) is systematic phase artifact, γ is the gyromagnetic ratio of hydrogen, and $T_c$ is the total time for which the current is applied.

In an embodiment, the modified Bloch equations are defined by $$S(k_x, k_y) = \int\int_{\Omega_{z_0}} M(x, y) e^{i[\gamma T_c B_z(x,y)]} e^{-i2\pi(k_x x + k_y y)} dxdy,$$

where M(x,y)>0 is the MR magnitude image of the slice Q located at $z_0$, δ(x,y) is systematic phase artifact, γ is the gyromagnetic ratio of hydrogen, and $T_c$ is the total time for which the current is applied In an embodiment, the sine wave has a lower power than the standard magnetic resonance electrical impedance tomography sequence.

In an embodiment, the sine wave is in a range of 15% to 30% of the power of the standard magnetic resonance electrical impedance tomography sequence.

In an embodiment, the standard magnetic resonance electrical impedance tomography sequence is a spin echo sequence.

In an embodiment, the multifrequency arbitrary-waveform constant-current source is configured to generate sine waves with frequencies between 100 Hz and 1 MHz.

In an embodiment, the multifrequency arbitrary-waveform constant-current source comprises a digital or analog multifrequency arbitrary-waveform signal source.

In an embodiment, the controller comprises a field programmable gate array (FPGA) controller.

In an embodiment, the controller comprises a function generator.

In an embodiment, a system for imaging biological tissue may comprise a controller or function generator, and a multifrequency arbitrary-waveform signal source with a digital-to-analog converter. In an embodiment, the controller or function generator is configured to generate a multifrequency magnetic resonance electrical impedance tomography sequence. In an embodiment, said generation may comprise producing, by the controller or function generator, a digital sequence, and converting, by the digital-to-analog converter, the digital sequence to an analog sequence. The generation may further comprise producing, by the digital-to-analog converter, a standard magnetic resonance electrical impedance tomography sequence based on the analog sequence. The generation may still further comprise producing, by the digital-to-analog converter, a sine wave at one or more predetermined frequencies. The generation may also comprise modulating the standard magnetic resonance electrical impedance tomography sequence with the sine wave.

In an embodiment, the multifrequency arbitrary-waveform signal source comprises a digital or analog multifrequency arbitrary-waveform signal source.

In an embodiment, the controller or function generator comprises a field programmable gate array (FPGA) controller or function generator.

In an embodiment, the system further comprises a magnetic resonance imaging system, wherein the magnetic resonance imaging system is configured to produce a measurable signal based on the multifrequency magnetic resonance electrical impedance tomography sequence.

In an embodiment, the measurable signal is interpreted using Bloch equations, wherein the Bloch equations are modified to include effects of external currents.

In an embodiment, the modified Bloch equations are defined by $$S(k_x, k_y) = \int_{\Omega_{z_0}} M(x, y) e^{i[\gamma T_c B_z(x,y)]} e^{-i2\pi(k_x x + k_y y)} dxdy,$$

where M(x,y)>0 is the MR magnitude image of the slice Q located at $z_0$, δ(x,y) is systematic phase artifact, γ is the gyromagnetic ratio of hydrogen, and $T_c$ is the total time for which the current is applied.

In an embodiment, the sine wave has a lower power than the standard magnetic resonance electrical impedance tomography sequence.

In an embodiment, the sine wave is in a range of 15% to 30% of the power of the standard magnetic resonance electrical impedance tomography sequence.

In an embodiment, the standard magnetic resonance electrical impedance tomography sequence is a spin echo sequence.

In an embodiment, the multifrequency arbitrary-waveform constant-current source is configured to generate sine waves with frequencies between 100 Hz and 1 MHz.

In an embodiment, a method of measuring an electrical property of a biological tissue at a frequency may comprise imaging the biological tissue using a system for imaging biological tissue as described herein. In certain embodiments, the frequency may be between about 100 Hz and about 1 MHz.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1:
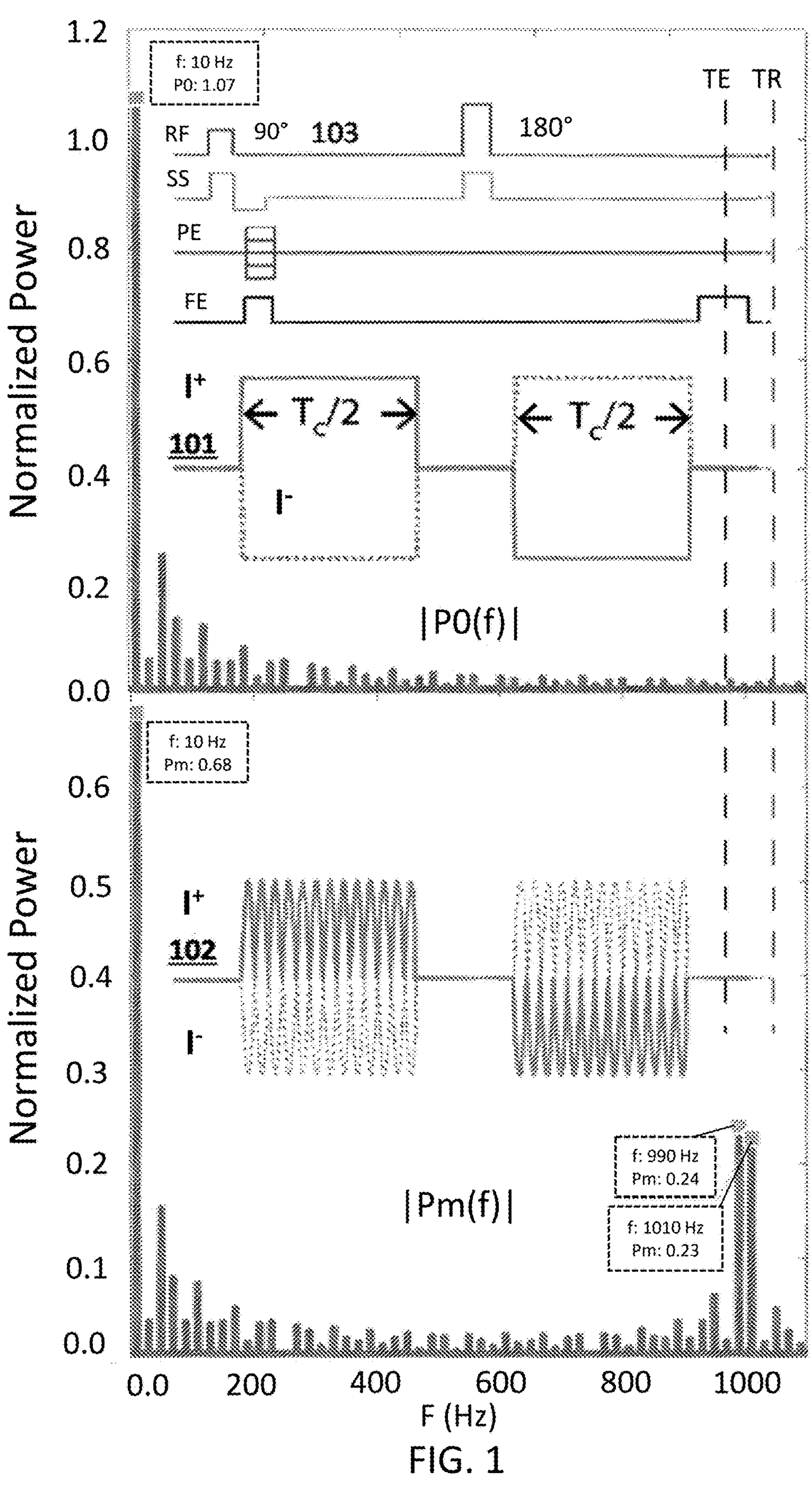
FIG. 1 depicts an illustrative example of a standard MREIT as compared to a multifrequency MREIT sequence, in accordance with an embodiment.

It is to be understood that the figures and descriptions of the present invention have been simplified to illustrate elements that are relevant for a clearer comprehension of the present invention, while eliminating, for the purpose of clarity, many other elements found in systems and methods of multifrequency magnetic resonance electrical impedance tomography. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "signal" is a reference to one or more signals and equivalents thereof known to those skilled in the art, and so forth.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art, all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components as well as the range of values greater than or equal to 1 component and less than or equal to 3 components. Similarly, a group having 1-5 components refers to groups having 0, 2, 3, 4, or 5 components, as well as the range of values greater than or equal to 1 component and less than or equal to 5 components, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

All percentages, parts and ratios are based upon the total weight of the compositions and all measurements made are at about 25° C., unless otherwise specified.

Referring now in detail to the drawings, in which like reference numerals indicate like parts or elements throughout the several views, in various embodiments, presented herein are systems and methods of multifrequency magnetic resonance electrical impedance tomography.

Disclosed herein are systems and methods that are based on existing MREIT techniques, but that expand the approach to include alternative current waveforms and MR imaging strategies to extract electrical spectral information. Specifically, the method creates high-resolution imaging of electrical conductivity distributions at frequencies between low and high frequencies, which enables non-invasive imaging of properties that will aid in cancer diagnosis and in the planning of cancer treatment, detection of tissue changes occurring during other disease processes or in characterization of the spectra of normal tissues or biosynthetic constructs.

It is not possible to use pure sinusoidal current waveforms in existing MREIT approaches. However, in certain embodiments, high-frequency components may be introduced by multiplying MREIT waveforms by higher-frequency rectified sine waves or other arbitrary waveforms. The resulting waveform modulation results in measurable differences in MREIT data as the modulation frequency is increased beyond critical dispersion points. In other embodiments, the method may use alternating current waveforms combined with diffusion weighted imaging to reconstruct changes in apparent diffusion and flow velocity caused by conduction.

In certain embodiments, a current source for generating a multifrequency Magnetic Resonance Electrical Impedance Tomography (MF-MREIT) imaging sequence may comprise a controller, a digital or analog multifrequency arbitrary-waveform signal source with a digital-to-analog converter (DAC), coupled to a Howland constant-current source. In some embodiments, the controller may comprise a field programmable gate array (FPGA) controller. In some embodiments, the controller may be replaced by a commercially-available function generator. In some embodiments, no constant-current source may be included and the DAC output of the controller may serve as the current source.

In an embodiment, a system for imaging biological tissue may comprise a controller, a multifrequency arbitrary-waveform constant-current source, a Howland constant-current source, and a digital-to-analog converter. In some embodiments, the controller may be configured to generate a multifrequency magnetic resonance electrical impedance tomography sequence. In certain embodiments, the generation may comprise producing, by the controller, a digital sequence, and converting, by the digital-to-analog converter, the digital sequence to an analog sequence. In some embodiments, the generation may further comprise producing, by the Howland constant-current source, a standard magnetic resonance electrical impedance tomography sequence based on the analog sequence. In certain embodiments, the generation may still further comprise producing, by the multifrequency arbitrary-waveform constant-current source, a sine wave at one or more predetermined frequencies. In some embodiments, the generation may also comprise modulating the standard magnetic resonance electrical impedance tomography sequence with the sine wave.

In some embodiments, the system may further comprise a magnetic resonance imaging (MRI) system (i.e., an MRI scanner). In certain embodiments, the MRI system may be configured to produce a measurable signal based on the multifrequency magnetic resonance electrical impedance tomography sequence. In some embodiments, the measurable signal may be interpreted using Bloch equations, as described herein. In an embodiment, the Bloch equations may be modified to include effects of external currents.

In some embodiments, the sine wave may have a lower power than the standard magnetic resonance electrical impedance tomography sequence. In an embodiment, the sine wave may have, for example, about 20% of the power of the standard magnetic resonance electrical impedance tomography sequence.

In certain embodiments, the standard magnetic resonance electrical impedance tomography sequence may be a spin echo sequence. In certain embodiments, the multifrequency arbitrary-waveform constant-current source may be configured to generate sine waves with frequencies between 100 Hz and 1 MHz.

In an embodiment, a method of measuring an electrical property of a biological tissue at a frequency may comprise imaging the biological tissue using a system for imaging biological tissue as described herein. In certain embodiments, the frequency may be between about 100 Hz and about 1 MHz. The frequency may be, for example, about 100 Hz, about 500 Hz, about 1,000 Hz, about 10,000 Hz, about 50,000 Hz, about 100,000 Hz, about 150,000 Hz, about 200,000 Hz, about 250,000 Hz, about 300,000 Hz, about 350,000 Hz, about 400,000 Hz, about 450,000 Hz, about 500,000 Hz, about 550,000 Hz, about 600,000 Hz, about 650,000 Hz, about 700,000 Hz, about 750,000 Hz, about 800,000 Hz, about 850,000 Hz, about 900,000 Hz, about 950,000 Hz, about 1 MHz, or any range between any two of these values, including endpoints.

Referring to FIG. 1, a standard MREIT sequence 101 and an MF-MREIT imaging sequence 102 are depicted, in accordance with the present disclosure. The standard MREIT sequence 101 is one repetition of a spin-echo (SE) imaging sequence. A unipolar current must be injected for as much of the sequence echo time (TE) as possible to maximize integrated phase, without overlapping radio frequency (RF) 103 or read gradients. If an SE sequence is used, the current polarity is reversed (i.e. from $I^+$ to $I^-$) after the 180° pulse to preserve signal.

The example standard MREIT sequence 101 total time is $T_c$ with a 64% duty cycle overlaid on an SE pulse sequence (TR=50 ms), and the normalized spectrum of the waveform showing its 10 Hz principal frequency. In some embodiments, to generate the MF-MREIT imaging sequence 102, the standard MREIT sequence 101 current envelope is modulated with a higher-frequency sine wave. In the depicted example, the sine wave has a frequency of 500 Hz.

It should be noted that standard MREIT sequence 101 depicted in FIG. 1 is merely an illustrative example of a standard MREIT sequence. A person of ordinary skill in art will understand that any other suitable MREIT sequence may be used and modulated with a higher frequency sine wave to form an MF-MREIT sequence.

In certain embodiments, an MRI scanner records the resulting field based on the imaging sequence. In some embodiments, the Bloch equations are used to interpret the recorded field information. In some embodiments, the Bloch equations for the standard sequence may be modified to include effects of external currents. In some embodiments, the interpreted MREIT data may contain information complementary to conventional MR images.

In accordance with an embodiment, the Bloch equations may be modified to:

$$S(k_x, k_y) = \int_{\Omega_{z_0}} M(x, y) e^{i[\gamma T_c B_z(x,y)]} e^{-i2\pi(k_x x + k_y y)} dx dy \tag{1}$$

where M(x,y)>0 is the MR magnitude image of the slice Q located at $z_0$, δ(x,y) is systematic phase artifact, γ is the gyromagnetic ratio of hydrogen, and $T_c$ is the total time for which the current is applied. After inverse Fourier transform, the MREIT phase images, $\phi(x,y)=B_z(x,y)\gamma T_c$, are then rescaled to produce $B_z$ images. In some embodiments, the standard deviation in $B_z$ data may be derived as:

$$sd(B_z) = \frac{1}{\sqrt{2}\,\gamma T_c Y} \tag{2}$$

where Y is the signal to noise ratio (SNR) of the magnitude image. Images obtained with positive (I+) and negative (I−) currents are complex divided to remove the systematic phase artifact δ.

Figure 2:
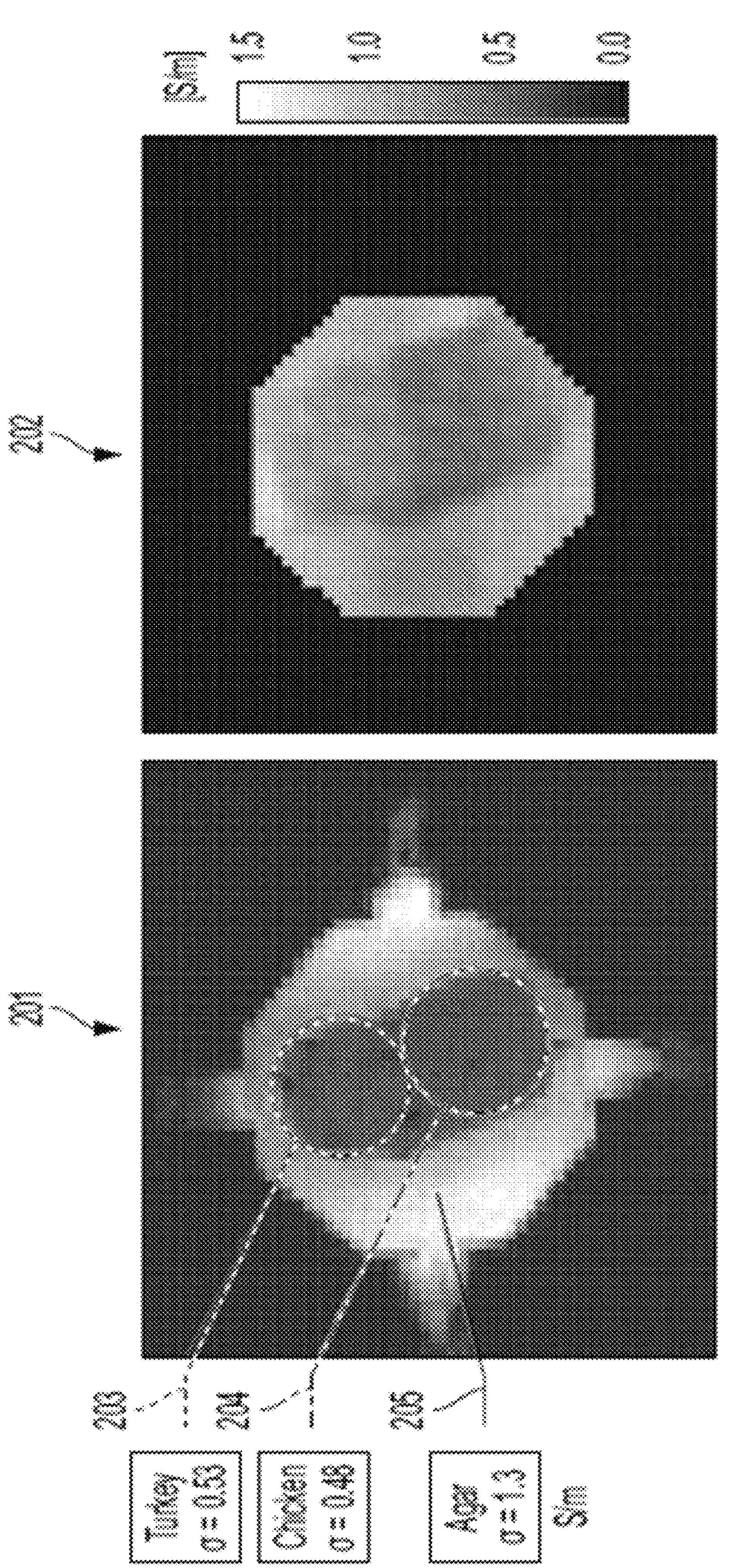
FIG. 2 depicts an illustrative example comparison of MREIT conductivity reconstruction in a phantom object, in accordance with an embodiment.

Referring to FIG. 2, an illustrative example comparison of MREIT conductivity reconstruction in a phantom object is depicted, in accordance with an embodiment. In the example, the two objects, a chicken breast muscle 204 and turkey breast muscle 203 in agar 205, were almost indistinguishable in SE magnitude images 201, but were well resolved in a quantitative conductivity image obtained by MREIT reconstruction 202, indicating that even standard MREIT images can provide valuable diagnostic information.

In certain embodiments, the characteristic frequency mix contained in MREIT imaging currents is determined by injection pulse width $T_c$ and the repetition time of the sequence (TR). Briefly referring back to FIG. 1, in the example, when polarity is reversed every 50 ms, the fundamental frequency will be 10 Hz. If this standard MREIT sequence 101 is modulated with a rectified 500 Hz sine wave MF-MREIT imaging sequence 102, the principal frequency is still at 10 Hz, but there is also power around 1 kHz. In some embodiments, the resulting modulation of MREIT waveforms may allow identification of tissue spectral properties. To achieve this result, in some embodiments, the power at the higher frequency range is only a percentage of the principal frequency, and data are integrated over time to form the phase signal, emphasizing lower-frequency spectral information. In some embodiments, the percentage is about 20%. In other embodiments, the fraction of the total power in secondary frequency components may be between about 15% and about 30% of the principal frequency. The fraction of total power may be, for example, about 15%, about 20%, about 25%, about 30%, or any range between any two of these values, including endpoints.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Figure 3:
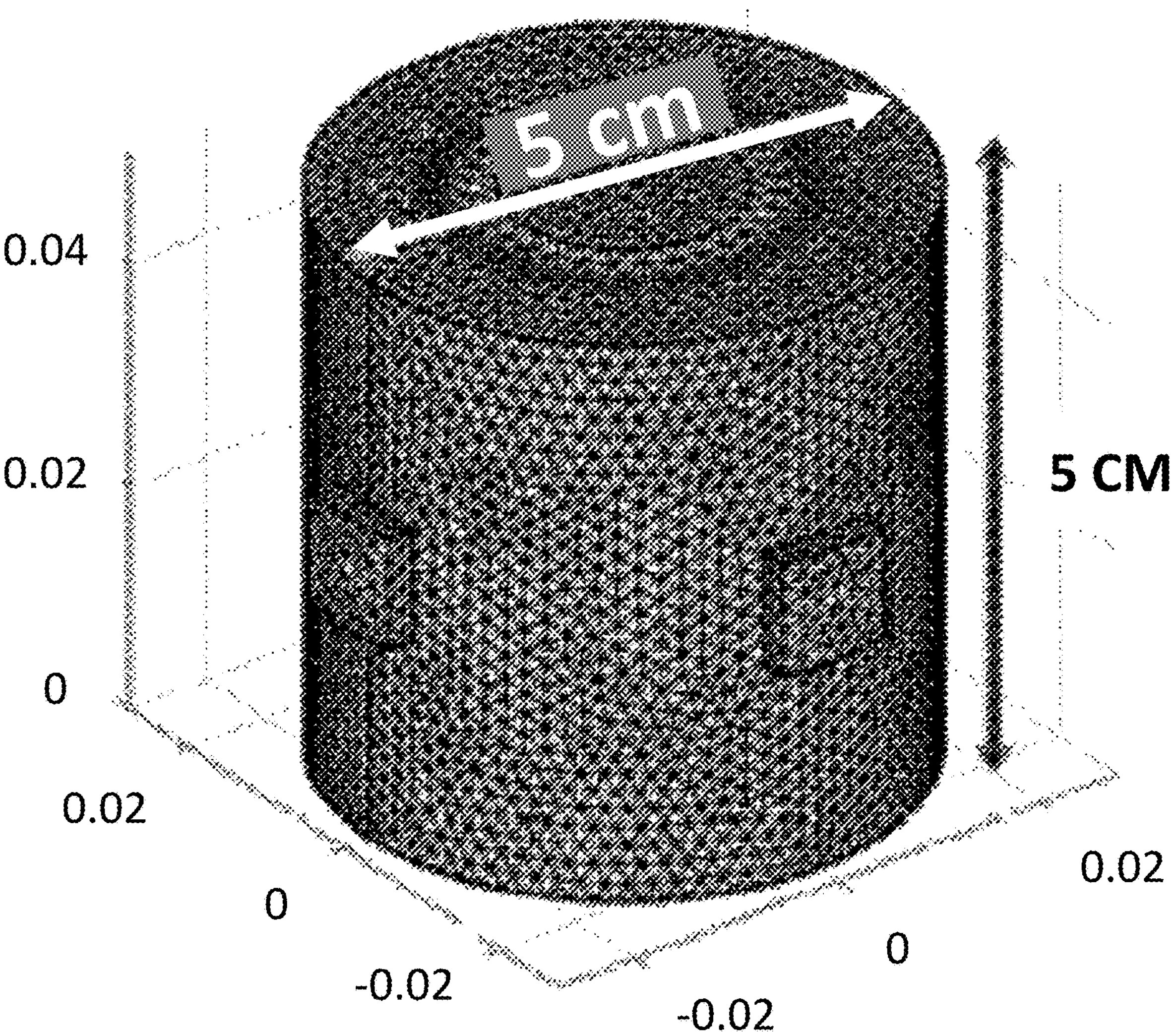
FIG. 3 depicts a three-dimensional finite element model containing a spherical membrane shell within an MREIT sample chamber, in accordance with the present disclosure.
Figure 4:
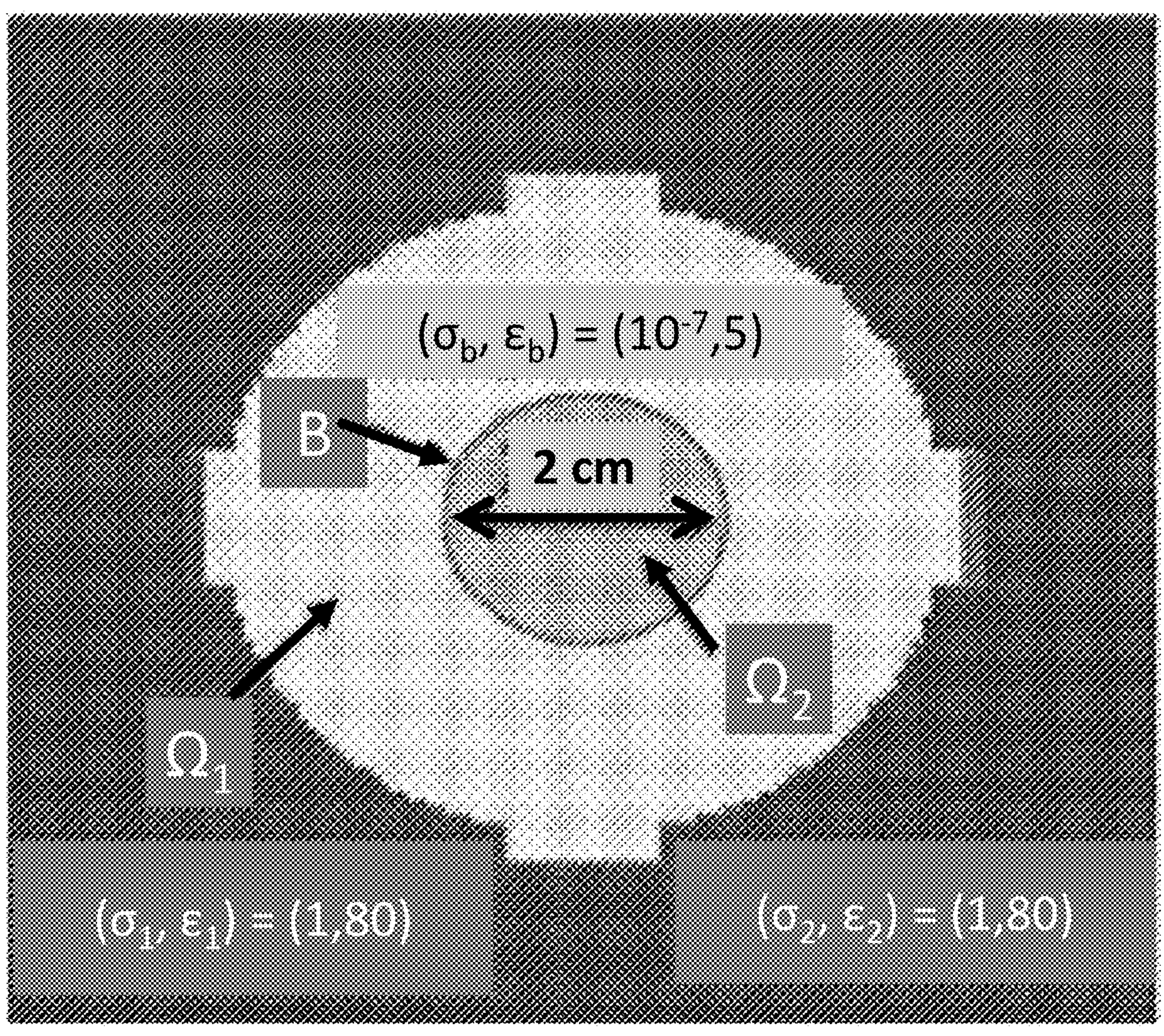
FIG. 4 depicts a two-dimensional model of a membrane of the element of FIG. 3, in accordance with the present disclosure.
Figure 5:
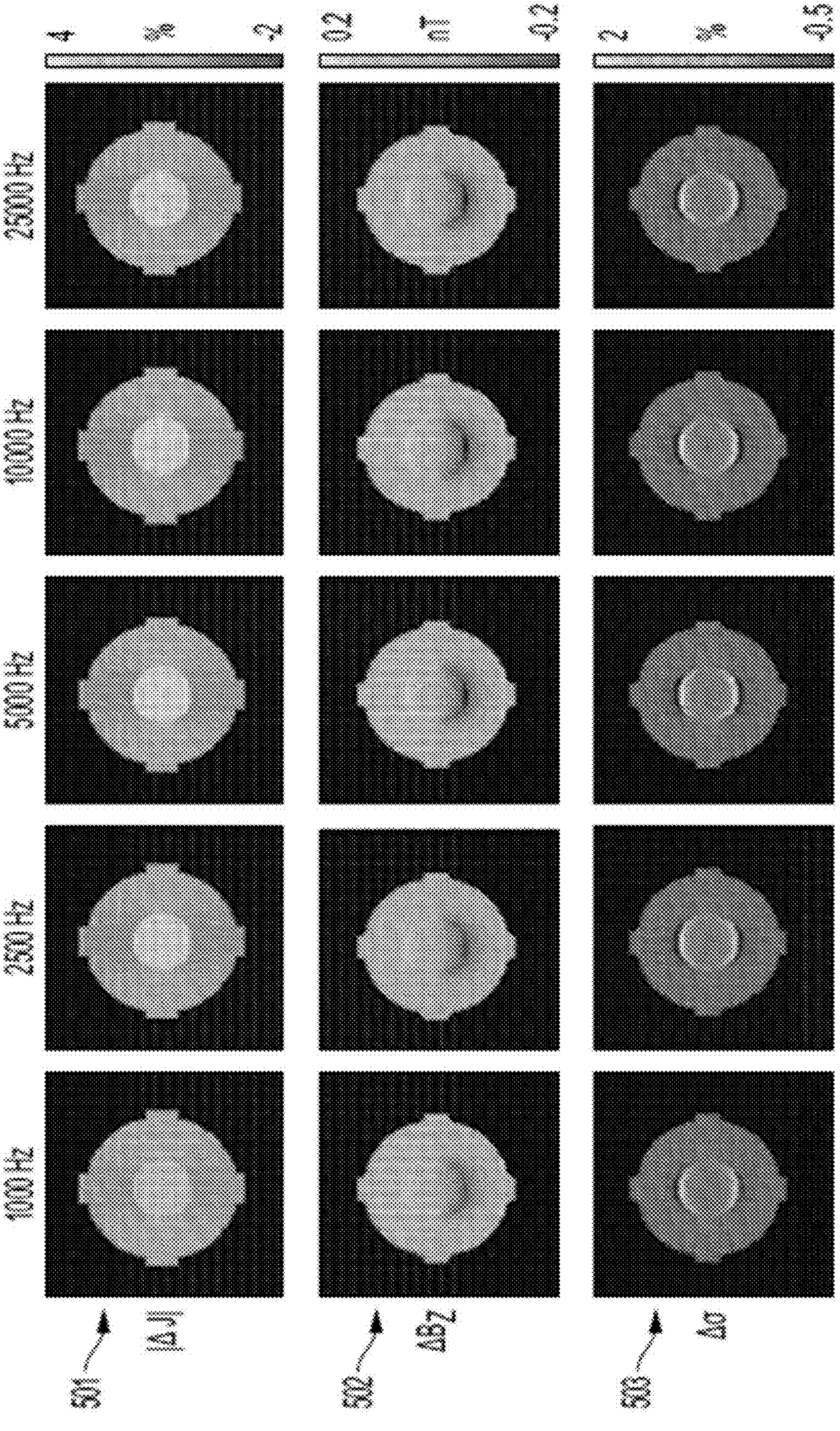
FIG. 5 depicts relative differences in current density magnitude ΔJ(top), $B_z$ (middle) and conductivity Δσ reconstructed using the Harmonic $B_z$ method (bottom) between simulated data at different MF-MREIT modulation frequencies and DC, in accordance with an embodiment.

Simulations were performed to determine the scale and distribution of potential size of MF-MREIT contrasts. Referring to FIG. 3, a three-dimensional finite element model containing a spherical membrane shell within an VIREIT sample chamber is depicted. FIG. 4 depicts a two-dimensional slice of said model. Fourier methods were used to generate solutions using MF-MREIT current waveforms modulated at up to 75 kHz. Computations were validated using time-dependent simulations. A peak current of 10 mA was used in all cases. As modulation frequency increased, proportionally more current penetrated the membrane, resulting in more uniform current density and $B_z$ distributions. Resulting absolute $B_z$ changes in MF-MREIT images from DC, and relative current density and reconstructed conductivities are shown for different modulation frequencies in FIG. 5. After accounting for factors relating to differences in waveform integrals, absolute changes in $B_z$ were above noise levels presently encountered in vivo in humans of around 0.05 nT. Current density increases (averaged within the spherical shell) were approximately 2.5% and averaged conductivity increases within the shell were about 1%.

While this simulation demonstrates the principle of MF-MREIT, it does not capture real tissue properties. In real tissue, conductivity increases, and permittivity decreases as a function of frequency, and the combined response could potentially be smaller. The simulation was therefore repeated using spectral characteristics of a spleen for the central sphere, and those of fat for the background, using Cole-Cole characteristics determined for each tissue. Spleen properties were used as both tumors as spleen are highly vascularized. Spleen has a low-frequency dispersion at around 50 Hz and a second large dispersion at around 10 MHz. Simulations showed for this case that averaged changes from DC for this more realistic case were much larger, around 3 nT in $B_z$, 2% in AJ and 3% in Au, respectively over the range 0 Hz to 75 kHz.

Figure 6:
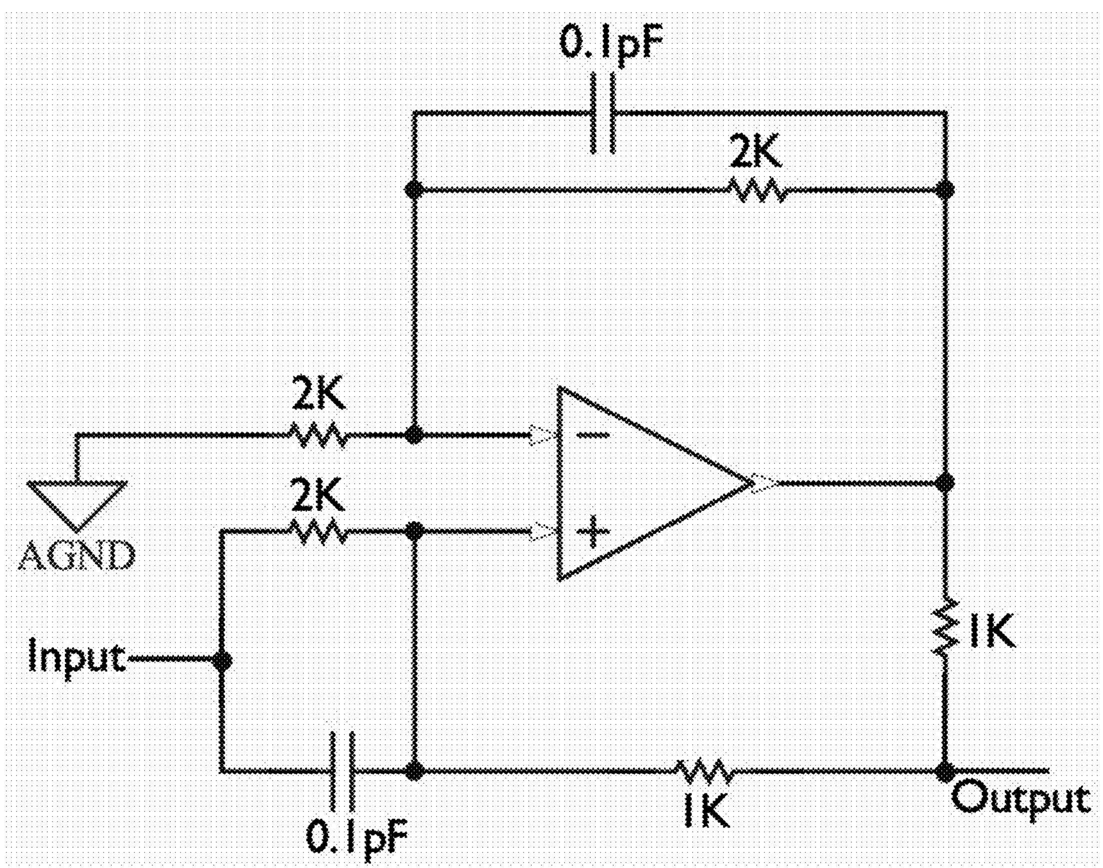
FIG. 6 depicts a circuit diagram for an exemplary Howland current source in accordance with an embodiment.
Figure 7:
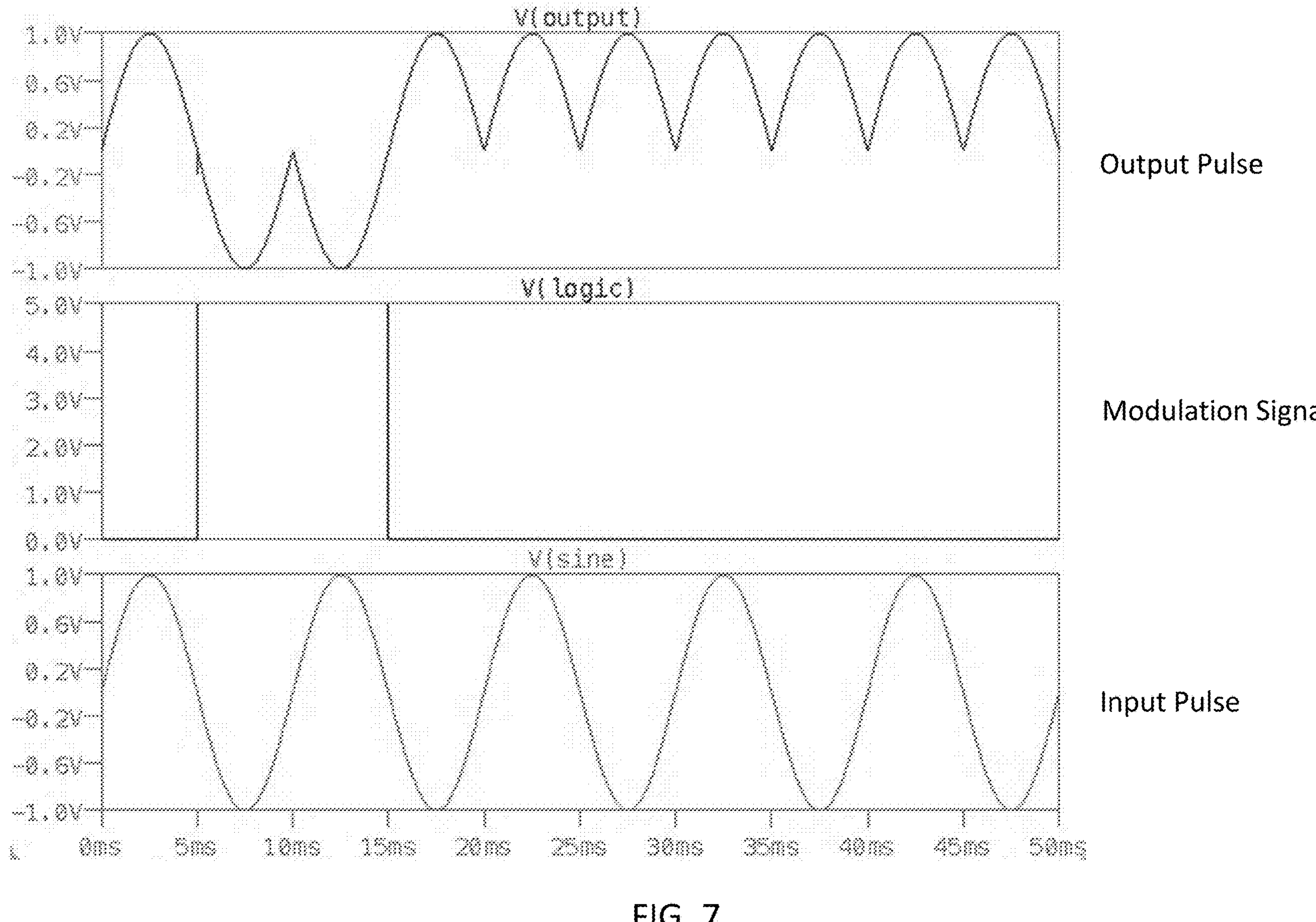
FIG. 7 depicts exemplary simulation signals in accordance with an embodiment.

FIG. 6 depicts a circuit diagram for an exemplary Howland source. The Howland source can provide for a high impedance (greater than 1 MΩ) current source or current sink. FIG. 7 depicts exemplary simulation signals comprising an input pulse, a modulation signal, and an output pulse.

Figure 8:
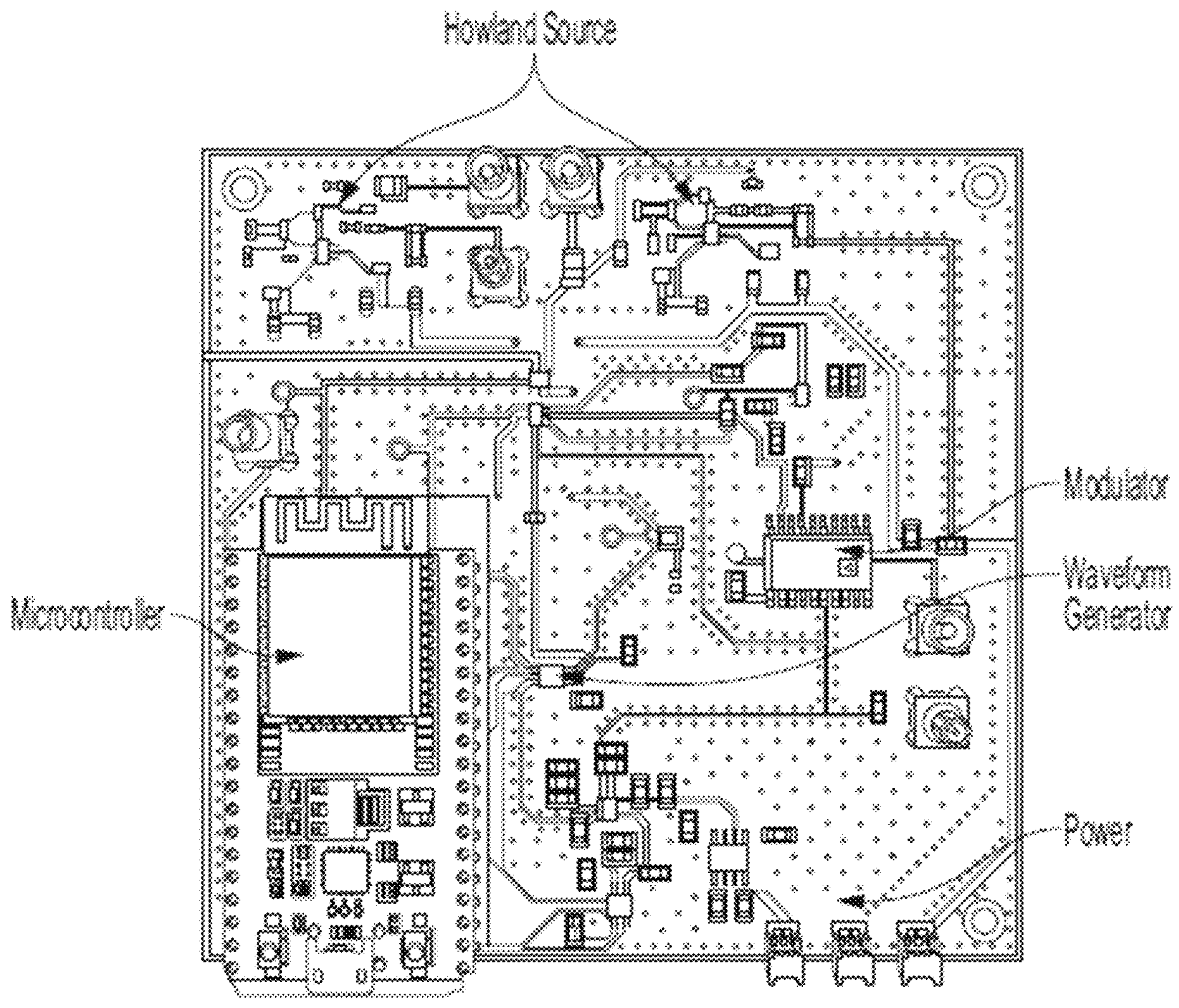
FIG. 8 depicts an image of an exemplary physical circuit used to perform multifrequency MREIT in accordance with an embodiment.
Figure 9:
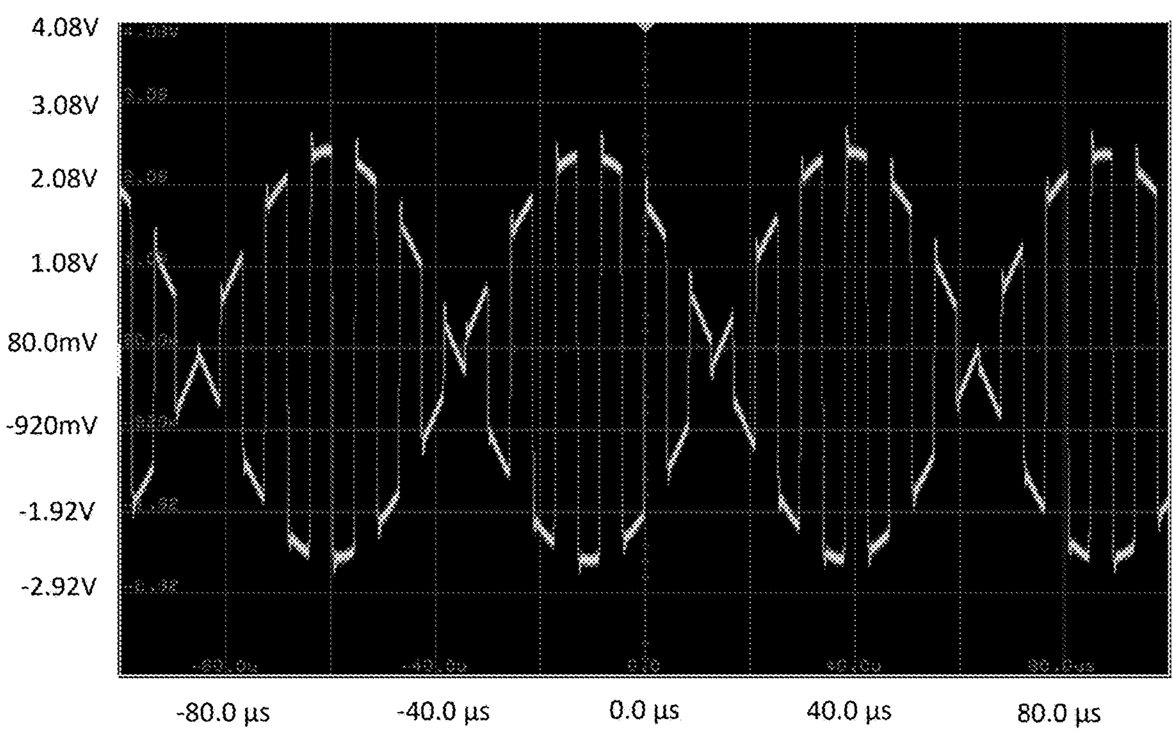
FIG. 9 depicts exemplary circuit bench test data in accordance with an embodiment.
Figure 9:
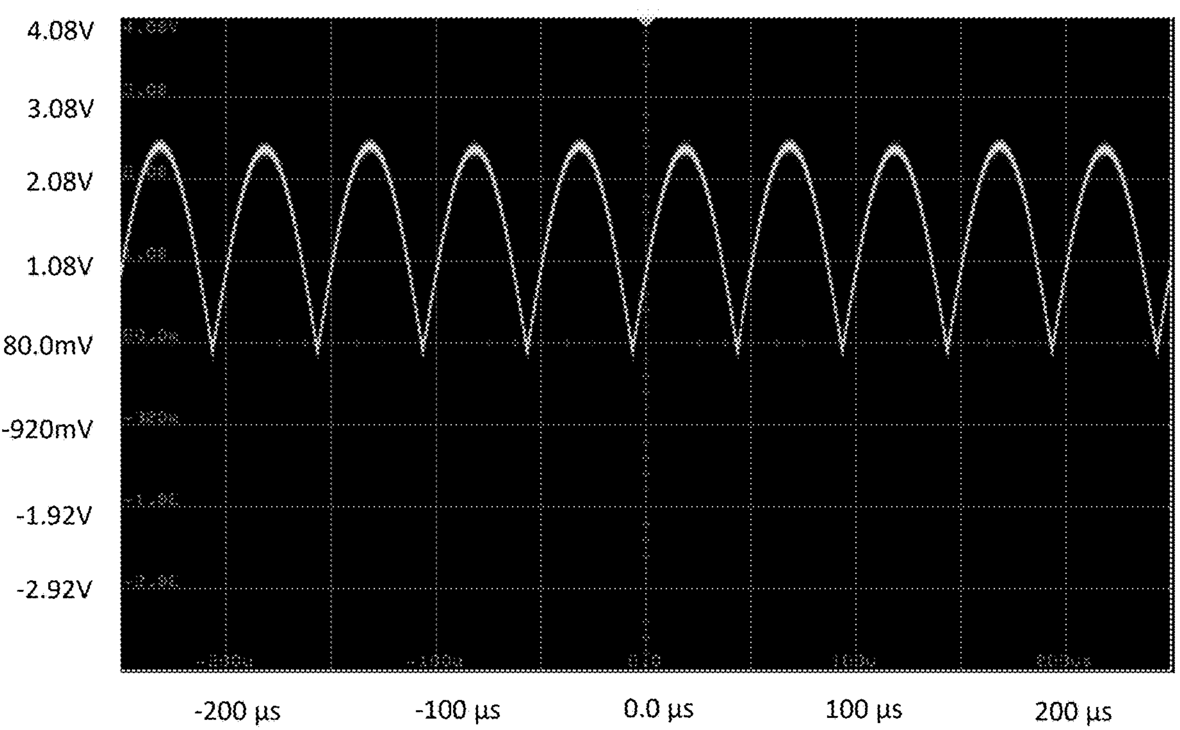

FIG. 8 depicts an image of an exemplary physical circuit used to perform multifrequency MREIT. The circuit includes a microcontroller, a power input, a waveform generator, a modulator, and a Howland source. FIG. 9 depicts exemplary circuit bench test data in accordance with an embodiment.

Computing Environment

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Figure 10:
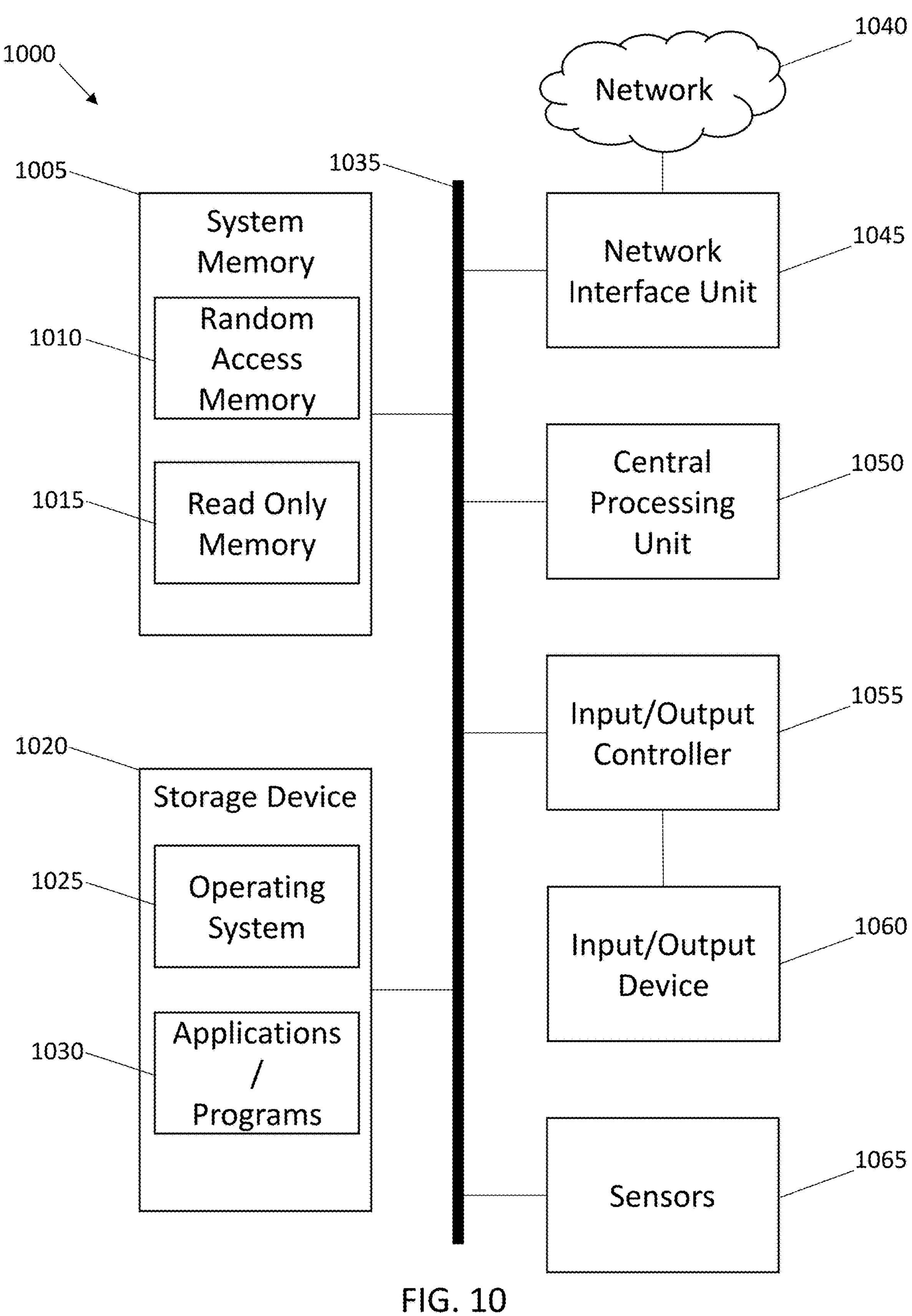
FIG. 10 depicts an exemplary computing environment in which aspects of the invention may be practiced.

FIG. 10 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 10 depicts an illustrative computer architecture for a computer 1000 for practicing the various embodiments of the invention. The computer architecture shown in FIG. 10 illustrates a conventional personal computer, including a central processing unit 1050 ("CPU"), a system memory 1005, including a random-access memory 1010 ("RAM") and a read-only memory ("ROM") 1015, and a system bus 1035 that couples the system memory 1005 to the CPU 1050. A basic input/output system containing the basic routines that help to transfer information between elements within the computer, such as during startup, is stored in the ROM 1015. The computer 1000 further includes a storage device 1020 for storing an operating system 1025, application/program 1030, and data.

The storage device 1020 is connected to the CPU 1050 through a storage controller (not shown) connected to the bus 1035. The storage device 1020 and its associated computer-readable media, provide non-volatile storage for the computer 1000. Although the description of computer-readable media contained herein refers to a storage device, such as a hard disk or CD-ROM drive, it should be appreciated by those skilled in the art that computer-readable media can be any available media that can be accessed by the computer 1000.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 1000 may operate in a networked environment using logical connections to remote computers through a network 1040, such as TCP/IP network such as the Internet or an intranet. The computer 1000 may connect to the network 1040 through a network interface unit 1045 connected to the bus 1035. It should be appreciated that the network interface unit 1045 may also be utilized to connect to other types of networks and remote computer systems.

The computer 1000 may also include an input/output controller 1055 for receiving and processing input from a number of input/output devices 1060, including a keyboard, a mouse, a touchscreen, a camera, a microphone, a controller, a joystick, or other type of input device. Similarly, the input/output controller 1055 may provide output to a display screen, a printer, a speaker, or other type of output device. The computer 1000 can connect to the input/output device 1060 via a wired connection including, but not limited to, fiber optic, ethernet, or copper wire or wireless means including, but not limited to, Bluetooth, Near-Field Communication (NFC), infrared, or other suitable wired or wireless connections.

As mentioned briefly above, a number of program modules and data files may be stored in the storage device 1020 and RAM 1010 of the computer 1000, including an operating system 1025 suitable for controlling the operation of a networked computer. The storage device 1020 and RAM 1010 may also store one or more applications/programs 1030. In particular, the storage device 1020 and RAM 1010 may store an application/program 1030 for providing a variety of functionalities to a user. For instance, the application/program 1030 may comprise many types of programs such as a word processing application, a spreadsheet application, a desktop publishing application, a database application, a gaming application, internet browsing application, electronic mail application, messaging application, and the like. According to an embodiment of the present invention, the application/program 1030 comprises a multiple functionality software application for providing word processing functionality, slide presentation functionality, spreadsheet functionality, database functionality and the like.

The computer 1000 in some embodiments can include a variety of sensors 1065 for monitoring the environment surrounding and the environment internal to the computer 1000. These sensors 1065 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

While the present disclosure has been illustrated by the description of exemplary embodiments thereof, and while the embodiments have been described in certain detail, the Applicant does not intend to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A system for imaging biological tissue, the system comprising:
- a controller;
- a multifrequency arbitrary-waveform constant-current source;
- a Howland constant-current source; and
- a digital-to-analog converter;
- wherein the controller is configured to generate a multifrequency magnetic resonance electrical impedance tomography pulse sequence, wherein said generation comprises:
  - producing, by the controller, a digital sequence;
  - converting, by the digital-to-analog converter, the digital sequence to an analog sequence;
  - producing, by the Howland constant-current source, a standard magnetic resonance electrical impedance tomography pulse sequence based on the analog sequence;
  - producing, by the multifrequency arbitrary-waveform constant-current source, a sine wave at one or more predetermined frequencies; and
  - modulating the standard magnetic resonance electrical impedance tomography pulse sequence with the sine wave at a frequency between 100 Hz and 1 MHz.

2. The system of claim 1, further comprising a magnetic resonance imaging system, wherein the magnetic resonance imaging system is configured to produce a measurable signal based on the multifrequency magnetic resonance electrical impedance tomography pulse sequence.

3. The system of claim 2, wherein the measurable signal is interpreted using Bloch equations, wherein the Bloch equations are modified to include effects of external currents, wherein the modified Bloch equations are defined by $$S(k_x, k_y) = \int\int_{\Omega_{z_0}} M(x, y) e^{i[\gamma T_c B_z(x,y)]} e^{-i2\pi(k_x x + k_y y)} dxdy,$$

where M(x,y)>0 is a MR magnitude image of a slice Q located at $z_0$, δ(x,y) is systematic phase artifact, γ is a gyromagnetic ratio of hydrogen, and $T_c$ is a total time for which the current is applied.

4. The system of claim 1, wherein a measurable signal of the sine wave comprises a lower power value than a measurable signal of the standard magnetic resonance electrical impedance tomography pulse sequence.

5. The system of claim 4, wherein the measurable signal of the sine wave is in a range of 15% to 30% of the power value corresponding to the measurable signal of the standard magnetic resonance electrical impedance tomography pulse sequence.

6. The system of claim 1, wherein the standard magnetic resonance electrical impedance tomography pulse sequence is a spin echo sequence.

7. The system of claim 1, wherein the multifrequency arbitrary-waveform constant-current source is configured to generate the sine wave.

8. The system of claim 1, wherein the multifrequency arbitrary-waveform constant-current source comprises a digital or analog multifrequency arbitrary-waveform signal source.

9. The system of claim 1, wherein the controller comprises a field programmable gate array (FPGA) controller or a function generator.

10. A system for imaging biological tissue, the system comprising:

a controller or function generator; and a multifrequency arbitrary-waveform signal source with a digital-to-analog converter;

wherein the controller or function generator is configured to generate a multifrequency magnetic resonance electrical impedance tomography pulse sequence, wherein said generation comprises:

producing, by the controller or function generator, a digital sequence;

converting, by the digital-to-analog converter, the digital sequence to an analog sequence;

producing, by the digital-to-analog converter, a standard magnetic resonance electrical impedance tomography pulse sequence based on the analog sequence;

producing, by the digital-to-analog converter, a sine wave at one or more predetermined frequencies; and modulating the standard magnetic resonance electrical impedance tomography pulse sequence with the sine wave at a frequency between 100 Hz and 1 MHz.

11. The system of claim 10, wherein the multifrequency arbitrary-waveform signal source comprises a digital or analog multifrequency arbitrary-waveform signal source.

12. The system of claim 10, wherein the controller or function generator comprises a field programmable gate array (FPGA) controller or function generator.

13. The system of claim 10, further comprising a magnetic resonance imaging system, wherein the magnetic resonance imaging system is configured to produce a measurable signal based on the multifrequency magnetic resonance electrical impedance tomography pulse sequence.

14. The system of claim 13, wherein the measurable signal is interpreted using Bloch equations, wherein the Bloch equations are modified to include effects of external currents, wherein the modified Bloch equations are defined by $$S(k_x, k_y) = \int\int_{\Omega_{z_0}} M(x, y) e^{i[\gamma T_c B_z(x,y)]} e^{-i2\pi(k_x x + k_y y)} dxdy,$$

where M(x,y)>0 is a MR magnitude image of a slice Q located at $z_0$, δ(x,y) is systematic phase artifact, γ is a gyromagnetic ratio of hydrogen, and $T_c$ is a total time for which the current is applied.

15. The system of claim 10, wherein a measurable signal of the sine wave comprises a lower power value than a measurable signal of the standard magnetic resonance electrical impedance tomography pulse sequence.

16. The system of claim 15, wherein the measurable signal of the sine wave is in a range of 15% to 30% of the power value corresponding to the measurable signal of the standard magnetic resonance electrical impedance tomography pulse sequence.

17. The system of claim 10, wherein the standard magnetic resonance electrical impedance tomography pulse sequence is a spin echo sequence.

18. The system of claim 10, wherein the multifrequency arbitrary-waveform constant-current source is configured to generate the sine wave.

19. A method of measuring an electrical property of a biological tissue at a frequency, the method comprising imaging the biological tissue using the system of claim 1.

20. A method of measuring an electrical property of a biological tissue at a frequency, the method comprising imaging the biological tissue using the system of claim 10.

* * * * *